United States Patent [19]

Poppelsdorf et al.

[11] Patent Number: 4,649,226

[45] Date of Patent: Mar. 10, 1987

[54] HYDROGENATION OF ALKYL OXALATES

[75] Inventors: Fedor Poppelsdorf, Charleston, W. Va.; Charles A. Smith, Myrtle Beach, S.C.

[73] Assignee: Union Carbide Corporation, Danbury, Conn.

[21] Appl. No.: 844,559

[22] Filed: Mar. 27, 1986

[51] Int. Cl.$^4$ .................. C07C 29/136; C07C 31/20
[52] U.S. Cl. ........................ 568/864; 502/527
[58] Field of Search ........................ 568/864

[56] References Cited

U.S. PATENT DOCUMENTS

| | | | |
|---|---|---|---|
| 4,022,715 | 5/1977 | Bornfriend | 252/463 |
| 4,042,738 | 8/1977 | Gulati | 428/116 |
| 4,112,245 | 9/1978 | Zehner et al. | 568/864 |
| 4,142,994 | 3/1979 | Alafandi | 252/450 |
| 4,366,093 | 12/1982 | Shiozaki et al. | 252/477 R |
| 4,440,873 | 4/1984 | Miyazaki et al. | 568/864 |
| 4,551,565 | 11/1985 | Miyazaki et al. | 568/864 |

FOREIGN PATENT DOCUMENTS

| | | | |
|---|---|---|---|
| 0060787 | 9/1982 | European Pat. Off. | 568/864 |
| 0097262 | 1/1984 | European Pat. Off. | 568/864 |

*Primary Examiner*—J. E. Evans
*Attorney, Agent, or Firm*—Steven T. Trinker

[57] ABSTRACT

An improved calcined hydrogenation catalyst shape which is useful for the catalysis of hydrogenation reactions in a tubular reactor is provided. The catalyst shape has an annular configuration with an open center core, and wherein the shape contains, as a reinforcing matrix distributed therein, up to about 50 percent by weight of milled glass fibers having specific dimensions and wherein the crush strength of the shape is vastly improved with little change in catalytic activity over the non-reinforced shape of comparable size. Additionally, when the shapes of the present invention are employed pressure-drop and diffusion problems are reduced. The catalyst shapes are particularly useful for the hydrogenation of alkyl oxalates to ethylene glycol whereby the reaction can be conducted at lower temperatures and hence by-product formation is minimized.

6 Claims, No Drawings

HYDROGENATION OF ALKYL OXALATES

FIELD OF THE INVENTION

This invention relates in general to improved hydrogenation catalyst shapes. In one aspect, this invention is directed to an improved hydrogenation catalyst in cylindrical form and having improved crush strength.

BACKGROUND OF THE INVENTION

It is well known in the art of chemical processing that catalysts can be prepared in a wide variety of shapes and sizes which will vary depending upon the particular reaction in which they are employed. For example, it is well known that the process of heterogeneous catalysts requires the presence of the catalyst in the form of discrete particles through which the reacting products may be passed under conditions necessary to effect the desired conversion. Depending upon the nature of the process, the discrete particles may be positioned in a fixed bed, moving bed or suspended in the reactants themselves as in a fluid bed process.

In some instances catalysts, such as compounds in the form of metals or other compositions, are required to be supported in their catalytic state since discrete particles in bulk form are neither sufficiently active or are so finely divided as not to be suitable for the intended use. A wide variety of catalytic supports are disclosed in the literature as well as processes for fabricating such supports and their use in chemical reactions.

Catalyst supports and the catalysts themselves can be fabricated in a wide variety of shapes and sizes with the optimum configuration depending upon the particular reaction in which the catalyst is employed. Batch operations may dictate the use of one type of supported catalyst whereas if the same reaction is conducted in continuous form a different configuration of the same catalyst may be preferred. Likewise, whether the reaction is effected in the liquid or gaseous state will of course, influence the choice of catalyst and particularly any support on which the catalyst may be contained.

Thus, one may find catalysts, both supported and unsupported, in the shape of discrete solid particles, porous particles, granules, spheres, microspheres, pellets, columns, rods, solid cylinders, hollow cylinders, porous sheets, screens meshes, honeycomb structures, and additional configurations or combinations thereof.

In many instances the mechanical strength of the catalyst or the support on which it is contained is not important and reaction conditions and reactants themselves are sufficiently mild so that the catalyst can be employed in a variety of shapes. For example, for some applications the catalyst can be prepared in situ or just prior to use and the structural strength or its particular configuration is not important.

However, for many reactions a serious problem can arise with shaped catalysts and catalyst supports if their structural strength is limited. For example, moving and shipping of catalysts which are prepared at a location other than the site at which they are used, in many instances requires that the catalyst or the support on which it is contained, be of sufficient structural integrity to withstand such motion. Additionally, charging and installing the catalysts to the catalyst zone of processing equipment and the motion of the equipment during operation can cause fragmentation of the catalyst and any supports with the production of unecessary particles or fines.

In moving bed processes the fines created due to fragmentation may be removed either in the existing fluid and unavoidably discharged into the air or sewage system. Conversely, in fixed bed processes which utilize such catalysts, the fines resulting from poor structural strength of the catalyst or support may lead to plugging of the reactor which requires shut down of the process and removal of the fines.

A variety of methods have been proposed in the literature for improving the structural and mechanical strength of catalysts and the supports on which they are contained. For example, in U.S. Pat. No. 4,142,994 which issued on Mar. 6, 1979 and is assigned to Filtros Corporation, there is disclosed and claimed mechanically and thermally stable porous calcined shaped catalyst supports in the form of particles which do not easily fragment as compared to structures previously known and composed of similar materials. In the disclosed process a clay is shaped, acid leached to a degree insufficient to destroy the plasticity of the clay, formed into shaped particles, and the calcined particles further extracted without impairing their shape. The resulting catalyst supports have high pore volume and surface area, and sufficient mechanical and thermal strength to minimize fragmentation.

Other methods have been reported in the literature for the fabrication of catalyst supports having improved properties. For example, in U.S. Pat. No. 4,042,738 which issued Aug. 16, 1977 and is assigned to Corning Glass Works, a support in the form of a honeycomb structure having a plurality of interconnected partitions is provided and which is indicated to possess high thermal shock resistance. It is also indicated in this patent that the particular geometry of the honeycomb disclosed was selected to avoid a rigid structure, since a mechanically stiff catalyst support which is not readily deformable does indeed have a high structural modulus, but consequently also has a low thermal shock resistance. Hence for the particular process in which the honeycomb structure is used, i.e., in a catalytic converter for emission control of internal combustion engines, a support is needed which has a low structural modulus and high thermal shock resistance.

It should also be noted that while improvements in the structural strength of catalytic supports are not difficult to achieve and can be accomplished by a variety of means, it is usually only done at the expense of the overall catalytic activity. For example, lowering the porosity by compressing or compactation will in some instances result in a support having a greater mechanical strength. However, the decreased porosity results in a corresponding decrease in surface area and hence the amount of available sites for catalysis to occur.

In U.S. Pat. No. 4,366,093 which issued Dec. 28, 1982 to K. Shiozaki et al of Japan, a cylindrical molded catalyst is disclosed for use in fixed bed reactors. The molded catalyst is indicated to have a low resistance to fluids, a large effective surface area good heat conductivity and sufficient mechanical strength for most applications. The novelty of the disclosed invention appears to reside in the geometric shape, size and configuration of the cylindrical molded catalyst. It is further indicated therein that it is necessary that the cylindrical molded catalyst have a specific size, that is, it must be from 3 to 6 mm in outer diameter, at least 1.0 mm in inner diameter, a wall thickness of at most 1.5 mm and a height of 3 to 6 mm. It is further indicated at column 2, lines 3–10 of the patent that no catalyst of this particular configuration had ever been prepared and put to practical use since it had been considered that a cylindrical catalyst of the shape indicated above, would have insufficient mechanical strength. The patentees further disclose at column 2, lines 21–23 that the compressive breaking strength in the direction of the diameter of the circle is at least 0.2 kg. It is further indicated that the materials used in the preparation of the cylindrical molded catalyst can be alumina, silica, or mixtures thereof and the catalytically effective material can be a metal salt or metal oxide such as copper halides, copper oxides and the like.

Hence prior to the present invention the catalysts, both supported and unsupported, disclosed in the literature were of a variety of shapes and sizes and in many instances custom made to serve the particular reaction conditions employed in the process being used. A catalyst support system of a particular configuration and shape which was useful for one type of process was not necessarily useful for others. Moreover, cylindrical molded catalysts as in the above patent did not always have sufficient crush strength to overcome the disadvantages noted and provide the optimum degree of catalytic activity. Efforts to improve the crush strength were directed largely to fabricating the cylindrical supports with thicker walls, or adding materials to the support which increased its mechanical strength. Catalyst supports which had increased wall thickness, resulted in a decrease in the inner core diameter and hence, a reduction in catalyst surface area. Catalyst supports which contained strengthening materials sacrificed a reduction in porosity and likewise a reduction in active surface area. What would be advantageous, would be a catalyst support which has sufficient structural integrity and yet which has no reduction in catalytic activity.

SUMMARY OF THE INVENTION

In its broad aspect the present invention relates to reinforced hydrogenation catalyst shapes which have improved structural and mechanical strength, particularly crush strength, over the non-reinforced catalyst shapes, which maintain excellent catalytic activity and which possess favorable pressure-drop and diffusion characteristics. The catalyst shapes of the present invention are particularly useful in commercial size tubular reactors wherein a minimum crush strength for annular shapes would be greater than about 4 pounds when a force is applied perpendicularly to the axis of the annulus, i.e., at right angles to the curved side of the shape.

The improved hydrogenation catalyst shapes of the present invention have an annular configuration with an open center core and wherein the shape contains as a reinforcing matrix distributed therein from about 10 to about 60 weight percent, based on the weight of the catalyst shape, of inert fibers having an average length of from about 0.03 to about 2 mm, and and an average diameter of from about 0.01 to about 0.02 mm. These catyalyst shapes have an overall dimension of up to about 8 mm in width, up to about 6 mm in thickness and an annular wall thickness of as low as 1.3 mm and a minimum crush strength of at least about 4 pounds as applied perpendicularly to the axis of the annulus.

DETAILED DESCRIPTION OF THE INVENTION

As previously indicated, the reinforced hydrogenation catalysts of the present invention are particularly useful in commercial tubular reactors wherein they exhibit desirable pressure-drop and diffusional characteristics compared to, for example, right angle solid cylinders of the same outside dimensions which have heretofore been employed. For example, the improved diffusional characteristics of the annular catalytic shapes also makes it possible to conduct hydrogenation reactions of alkyl oxalates at lower temperatures which minimize by-product formation as a result of degradation of the reaction product ethylene glycol.

By the term "catalyst shapes" or "shapes" as employed throughout the specification and appended claims is meant the catalyst composition itself which can exist in the annular shape, or the catalyst contained on, or in a support and wherein the support can be inert, an adjuvant or catalytically active itself.

The crush strength of hydrogenation catalyst shapes in annular form and having a center core, can be greatly enhanced by the incorporation into the shapes prior to calcination, of fibers having a particular length and thickness as hereinafter indicated. In practice, it has been found that when fibers, such as milled glass fibers, are incorporated into the catalyst shapes, that not only is the crush strength vastly improved, but that the pressure-drop and diffusion characteristics are also enhanced. Moreover, it has also been noted that the catalytic activity of the shapes is is at least comparable to that of the non-reinforced ones.

As previously indicated, the fibers which are employed in the catalytic shapes of the present invention are fibers, preferably milled glass fibers, which have specific dimensions and which are employed in the annular shape in specified amounts. For example, the fibers should have a length of from about 0.03 to about 2 mm and a thickness of from about 0.005 mm to about 0.03 mm. Particularly preferred fibers are those having a length of up to about 1.0 mm and a diameter of from about 0.01 to about 0.02 mm. Optimum results have been obtained when the fibers have a length of up to 1.0 mm and a diameter of about 0.01375 mm. Milled glass fibers having the above dimensions are available from Owens-Corning under code number 72J52028 and have a regular distribution of lengths from about 0.793 mm to about 0.038 mm (1/32" to 0.0015").

Although milled glass fibers of the indicated length and thickness are preferred, other inert, inorganic fibers having the same dimensions can also be employed in the catalytic shapes of the present invention. For example, inorganic fibers such as those composed of aluminum or other metal oxides can be used. It is of course necessary that the particular fiber chosen does not adversely affect the reactants, catalyst or support and do in fact provide the desired reinforcement to improve the crush strength of the annular shapes. However, for economic reasons milled glass fibers of the dimensions indicated above are ideally suited for use in the shapes of the present invention.

The quantity of fibers employed in the annular shapes can vary but for the most part they can be comprise up to about 50 percent by weight based on the total weight of the catalyst. In view of the fact that the annular shapes of the present invention can contain a relatively large amount of fibers one would expect that the catalytic activity of a comparably shaped catalyst without the fibers would have a markedly superior activity to those of this invention which have less of the active catalytic component. However, it was unexpectedly and surprisingly found that the incorporation of the fibers into the shapes does not materially effect the activity when compared with a similar shape having no fibers.

It has been observed that the crush strength of annular shapes without reinforcement typically is not much different before and after calcination. For instance, it has been noted that an annular shape which had not been reinforced had an average crush strength of 4.1 pounds with a standard deviation of 0.5 prior to calcination and after calcination a crush strength of 4.4 pounds standard deviation of 0.6 Conversely, for a closely similar shape containing 22.5 weight percent of milled glass fibers, 1/32" in size, the crush strength was 4.2 pounds before calcination and an average 7.5 pounds per square inch after calcination at 750° C. for 5 hours in air. The annular shapes which can be prepared in accordance with the teachings of the present invention and which are particularly useful for the hydrogenation of alkyl oxalates in tubular reactors, have approximate dimensions of 8×5 mm with a 2.4 mm core and are reinforced with 25 weight percent of milled glass fibers having an average diameter of about 0.01375 mm. Such annular shapes fabricated in accordance with this invention exhibit enhanced crush strengths both before and after calcining. For example, an annular shaped composition comprised of copper or silica and fabricated with the above dimensions had an average crush strength of 7.5 pounds per square inch before calcination and an average crush strength of 12.0 pounds per square inch after calcination.

As indicated above, the improved hydrogenation catalyst shapes of the present invention are particularly useful for hydrogenation reactions conducted in tubular reactors. The preferred catalyst for the hydrogenation of alkyl oxalates, such as the lower alkyl oxalates, e.g., methyl, ethyl, butyl, to ethylene glycol is copper contained on silica. Catalyst shapes comprised of this composition can be conveniently prepared by methods known in the art. In the present invention the fibers are incorporated into the catalyst composition prior to fabrication into the annular shapes and prior to calcination. A variety of methods can be used to incorporated and evenly distribute the fibers throughout the catalyst composition and which will be determined, in part, by the methods employed in the fabrication of the annular shapes. For most practical purposes the fibers can be blended into the initial mixture containing, for example, a compound of one or more catalytically active metals deposited on silica and other additives such as lubricants for example, graphite, and the like. Thereafter, the mixture can be tableted, molded, extruded, or compressed into annular shapes, and calcined in air in accordance with known procedures at temperatures of at least about 750° C. for a period of at least 5 hours.

In a preferred process, the catalyst mixture can be fabricated into annular shapes of the desired configuration by tableting procedures. In contrast to prior art shapes formed by tablet making which are either structurally weak due to an open pore structure and insufficient compaction, or are too compact due to a high degree of compression, the shapes of the present invention have excellent pressure-drop and diffusion properties.

The reinforced catalyst shapes of the present invention are particularly useful in commercial tubular hydrogenation reactors for the manufacture of ethylene glycol from dimethyl oxalate. In such reactors hydrogenation is effected in the presence of an appropriate catalyst, such as copper on silica, at a temperature of about 170° C., to about 230° C., and at a liquid hourly space velocity (LHSV) of 0.1 to 3.0 and at a gas hourly space velocity (GHSV) of 2000 to 2500.

The following examples are illustrative:

EXAMPLE 1

Annular catalyst shapes were prepared both with and without glass fiber reinforcements and calcined at 750° C. in air for five hours. The reinforced shapes contained between 18.37 and 25.0 weight percent of milled glass fibers having diameters of 0.0175 mm and 0.01375 mm and a regular distribution of lengths of from about 0.04 mm to about 0.8 mm. Crush strengths were measured on samples both before and after calcination and with and without glass fiber reinforcement. The results obtained are set forth in Table I below:

TABLE I

| | | CRUSH STRENGTH OF CALCINED COPPER-SILICA CATALYST ANNULAR SHAPES | | | |
|---|---|---|---|---|---|
| | | CRUSH STRENGTH[1], (STANDARD DEVIATION) | | | |
| | WT % | BEFORE CALCINATION | | AFTER CALCINATION | |
| EXAMPLE | FIBERS | FIBERS | NO FIBERS | FIBERS | NO FIBERS |
| 1 | 0 | | 4.13(0.52) | | 4.4(0.61) |
| 2 | 18.7 | 4.2(0.46) | | 7.3(1.13) | |
| 3 | 0 | | 5.75(0.54) | | 8.1(1.4) |
| 4 | 18.37 | 5.70(0.54) | | 10.45(1.32) | |
| 5 | 0 | | 4.35(0.04) | | 6.0(1.15) |
| 6 | 18.37 | 4.5(0.45) | | 7.25(0.43) | |
| 7 | 0 | | 5.1(0.8) | | 6.5(1.7) |
| 8 | 18.37 | 5.1(0.8) | | 7.6(1.5) | |
| 9 | 25.0 | 7.5(1.01) | | 12.0(1.27) | |
| 10 | 25.0 | 7.8(1.18) | | 12.7(2.24) | |
| 11 | 25.0 | 4.0(0.23) | | 8.3(1.22) | |
| 12 | 25.0 | 6.2(1.83) | | 8.93(1.02) | |
| 13 | 25.0 | 6.0(6.25) | | 7.20(0.36) | |
| 14 | 50 | 4.1(0.56) | | 8.53(0.83) | |
| 15 | 25.0 | 5.9(1.23) | | 8.10(1.00) | |

TABLE I-continued

CRUSH STRENGTH OF CALCINED COPPER-SILICA CATALYST ANNULAR SHAPES

| | | CRUSH STRENGTH[1], (STANDARD DEVIATION) | | | |
|---|---|---|---|---|---|
| | WT % | BEFORE CALCINATION | | AFTER CALCINATION | |
| EXAMPLE | FIBERS | FIBERS | NO FIBERS | FIBERS | NO FIBERS |
| 16 | 0 | | 5.2(0.85) | | 6.43(1.28) |

Note: Examples 2, 4 and 6 employed fibers having a diameter of 0.0175 mm and the remaining examples used fibers of 0.01375 mm diameter. Weight percent of milled glass fibers is before calcination.
[1]pounds; average of 15 determinations.

EXAMPLE 2

A comparison of the activity was made of reinforced and non-reinforced calcined copper on silica catalyst compositions in a bench-scale laboratory hydrogenation unit for the hydrogenation of dimethyl oxalate to ethylene glycol. The reinforced catalyst composition contained 18.4 weight percent of milled glass fibers. Examples 17 and 18 used 0.0175 mm diameter fibers whereas examples 21 and 22 used fibers having a diameter of 0.01375 mm. Examples 17 and 19 used copper on silica material prepared from an ammonium ion-stabilized silica sol whereas examples 18, 20, 21, 22, 23, and 24 employed copper on silica material prepared from sodium ion-stabilized solutions. All samples were calcined at 750° C. in air for five hours before use. For accuracy in comparing the activity the catalyst shapes employed were crushed and classified into 1 to 2 mm particles. The results obtained are set forth in Table II below:

TABLE II

COMPARISON OF CATALYTIC ACTIVITY

| Example | Reinforced | | Non-reinforced | | Reinforced | | Non-reinforced | |
|---|---|---|---|---|---|---|---|---|
| | 17 | 18 | 19 | 20 | 21 | 22 | 23 | 24 |
| Time on catalyst, hrs. | 7.0 | 9.0 | 7.0 | 9.0 | 6.0 | 8.0 | 6.0 | 8.0 |
| Mole ratio H/oxalate | 113 | 111 | 113 | 114 | 107 | 105 | 109 | 109 |
| Ethylene glycol yield | 88.9 | 82.2 | 25.5 | 61.5 | 55.6 | 70.8 | 33.8 | 59.1 |
| Efficiency | 89.4 | 82.5 | 25.5 | 61.5 | 55.6 | 70.8 | 33.8 | 59.1 |

In experiments conducted using the reinforced catalyst shapes of the present invention it was confirmed that calcined annular shapes reinforced with 25 weight percent of milled glass fibers and reduced to 9 to 16 mesh (1 to 2 mm) fragments are about as active catalytically for the hydrogenation of dimethyl oxalate as the non-reinforced material. This was indeed unexpected and surprising since, a priori, there is a 25 percent less active material in the same volume of the reinforced composite.

Although the invention has been illustrated by the preceding examples it is not to be construed as being limited to the materials employed therein, but rather the invention encompasses the generic area as hereinbefore disclosed. Various modifications can be made without departing from the spirit and scope thereof.

What is claimed is:

1. A process for the hydrogenation of alkyl oxalates to ethylene glycol in a tubular reactor and in the presence of a bed of hydrogenation catalyst packed in a tubular column, which comprises effecting said hydrogenation reaction under hydrogenation conditions in the presence of the improved calcined hydrogenation catalyst shape having an annular configuration with an open center core, and wherein said shape contains, as a reinforcing matrix distributed therein, from about 10 to about 60 weight percent, based on the total weight of said catalyst shape, of fibers having a regular distribution of lengths of from about 0.04 mm to about 2.0 mm, and an average diameter of from about 0.005 mm to about 0.03 mm, said annular catalyst shape having overall dimensions of up to about 10 mm in width, from about 2.3 mm up to about 10 mm in thickness, a wall thickness as measured from the core to the outer circumference of said annular shape of as low as 1.3 mm, and a minimum crush strength of at least about 4 pounds as applied perpendicularly to the axis of the annulus.

2. The process of claim 1 wherein the hydrogenation catalyst comprises copper on silicon dioxide.

3. The process of claim 2 wherein the fibers are milled glass fibers.

4. The process of claim 1 wherein said alkyl oxalate is dimethyl oxalate.

5. The process of claim 1 wherein said hydrogenation is carried out at from about 170° C. to about 230° C.

6. The process of claim 1 wherein the LHSV is from 0.1 to 3.0 and the GHSV is from 2000 to 2500.

* * * * *